United States Patent
Wasserscheid et al.

(10) Patent No.: US 6,900,313 B2
(45) Date of Patent: May 31, 2005

(54) CHIRAL IONIC LIQUIDS

(76) Inventors: Peter Wasserscheid, Grevenbroicher Strasse 2, Köln (DE), 50829; Wilhelm Keim, Brüsseler Ring 90, Aachen (DE), 52074; Carsten Bolm, Nizzaallee 44, Aachen (DE), 52072; Andreas Bösmann, Düppelstrasse 118, Aachen (DE), 52068

( * ) Notice: Subject to any disclaimer, the term of this patent is extended or adjusted under 35 U.S.C. 154(b) by 22 days.

(21) Appl. No.: 10/182,388
(22) PCT Filed: Jan. 29, 2001
(86) PCT No.: PCT/EP01/00924
§ 371 (c)(1), (2), (4) Date: Dec. 27, 2002
(87) PCT Pub. No.: WO01/55060
PCT Pub. Date: Aug. 2, 2001

(65) Prior Publication Data
US 2003/0149264 A1 Aug. 7, 2003

(30) Foreign Application Priority Data
Jan. 28, 2000 (DE) .......................... 100 03 708

(51) Int. Cl.[7] ................. C07D 277/04; C07D 277/08; C07D 263/02; C07D 413/00; C07D 233/00
(52) U.S. Cl. ................. 544/59; 544/108; 544/404; 548/145; 548/215; 548/300.1; 564/282; 564/290; 564/291; 564/292; 564/295; 564/296
(58) Field of Search ................. 544/59, 108, 404; 548/146, 215, 300.1, 300.7; 564/282, 290, 291, 292, 295, 296

(56) References Cited

PUBLICATIONS

Hawley's Condensed Chemical Dictionary, 12th ed., Richard J. Lewis, Sr., © 1993 by Van Nostrand Reinhold. p. 594.*

Concise Chemical Dictionary, edited by Drs. Hans–Dieter Jakubke and Hans Jeschkeit, © 1993 by Walter de Gruyter & Co., p. 490.*

McGraw–Hill Dictionary of Chemical Terms, 3rd ed. edited by Sybil P. Parker, © 1984 McGraw–Hill, Inc., p. 200.*

Wassercheid and Keim, "Ionic Liquids—New 'Solutions' for Transition Metal Catalysis" Angewandte Chemie International Edition, vol. 39 pp. 3772–3789 (2000).*

Turner et al, "Use of ab Initio Calculations toward the Rational Design of Room Temperature Ionic Liquids" J. Phys. Chem. A v 107, pp. 2277–2288 (2003).*

Wu and Zhang, "Enantioselective synthesis of alpha–amino acids in chiral reverse micelles" Tetrahedron: Asymmetry, vol. 9, pp. 1441–1444 (1998).*

The Merck Index, 13th ed., p. 639, entry # 3639 "Ephedrine" Merck & Co., Whitehouse Station, NJ (2001).*

Vo Thanh et al "Solvent–Free Microwave–Assisted Preparation of Chrial Ionic Liquids from (–)–N–Methylephedrine" European Journal of Organic Chemistry, issue 5, pp. 1112–1116 (2004).*

Howarth et al, "Moisture Stable Dialkylimidazolium Salts as Heterogeneous and Homogeneous Lewis Acids in the Diels–Alder Reaction" Tetrahedron Letters, vol. 38(17), pp. 3097–3100 (1997).*

* cited by examiner

*Primary Examiner*—Richard L. Raymond
*Assistant Examiner*—Zachary C. Tucker
(74) *Attorney, Agent, or Firm*—John S. Child, Jr.; Patrick J. Hagan

(57) ABSTRACT

The invention relates to chiral ionic liquids of the general formula $$[A]_n{}^+[Y]^{n-},$$

whereby n=1 or 2, the anion $[Y]^{n-}$ is the anion of an organic or inorganic proton acid and the cation $[A]^+$ an optically active organic ammonium cation with up to 50 carbon atoms, at least one chirality center and at least one functional group that can produce a coordination by forming hydrogen bridges or by providing free electron pairs. At least one chirality center is provided with a distance of up to 5 atomic bonds from the functional group. The invention also relates to a method for producing said chiral ionic liquids and to the use thereof in methods for the asymmetric synthesis, the asymmetric catalysis and for separating racemates.

22 Claims, No Drawings

CHIRAL IONIC LIQUIDS

CROSS-REFERENCE TO RELATED APPLICATIONS

This Application is a national phase filing of co-pending International Application No. PCT/EP01/00924 filed Jan. 29, 2001, which claims the benefit of that application under 35 U.S.C. § 120 and which also claims the benefit under 35 U.S.C. § 119 of German Application No. 100 03 708.9 filed Jan. 28, 2000.

This invention relates to chiral ionic liquids, a method for producing them and their use in methods for asymmetric synthesis, asymmetric catalysis and for separating racemates.

Ionic liquids are generally understood to be salts or mixtures of salts, whose melting points are below 80° C. These salts comprise anions such as e.g. halogenostannates, halogenoaluminates, hexafluorophosphates or tetrafluoroborates combined with substituted ammonium, phosphonium, pyridinium or imidazolium cations. A number of publications already describe the use of ionic liquids as solvents for transition metal-catalysed reactions (T. Welton, Chem. Rev. 1999, 99, 2071; J. D. Holbry, K. R. Seddon, Clean Products and Processes, 1999, 223). For example hydrogenation of olefins with rhodium(I) (P. A. Z. Suarez, J. E. L. Dullius, S. Einloft, R. F. de Souza and J. Dupont, Polyhedron 15/7, 1996, 1217–1219), ruthenium(II) and cobalt(II) complexes (P. A. Z. Suarez, J. E. L. Dullius, S. Einloft, R. F. de Souza and J. Dupont, Inorganica Chimica Acta 255, 1997, 207–209) was performed successfully in ionic liquids with tetrafluoroborate anion. Hydroformylation of functionalized and unfunctionalized olefins with rhodium catalysts in ionic liquids with weakly coordinating anions (e.g. $PF_6^-$, $BF_4^-$) is also described (EP-A-0776880, Y. Chauvin, L. Mussmann, H. Olivier, Angew. Chem., [Applied Chem.] Int. Ed. Engl., 1995, 34, 2698; W. Keim, D. Vogt, H. Waffenschmidt, P. Wasserscheid, J. of Cat., 1999, 186, 481).

A two-stage method for synthesis of binary ionic liquids of the $[A]^+[Y]^-$ type can be used (J. S. Wilkes, M. J. Zaworotko, J. Chem. Soc., Chem. Commun., 13, 1992, 965). At the same time the organic ammonium salt $[NR^1R^2R^3R]^+ X^-$ or the organic phosphonium salt $[PR^1R^2R^3R]^+X^-$ is first synthesized by reaction of an alkylating reagent RX and an amine $NR^1R^2R^3$ or a phosphane $PR^1R^2R^3$ in a quarternising reaction. $X^-$ is generally a halide ion. The organic halide salt is isolated and converted in a subsequent, second reaction step in an exchange reaction with the alkali or alkaline earth salt of the $M^+[Y]^-$ type. This occurs in a solvent in which the by-product $M^+X^-$ is difficult to dissolve, whereas the ionic liquid $[A]^+[Y]^-$ to be synthesized is easily dissolved.

This two-step method was used with success in the literature for depicting ionic liquids with $[BF_4]^-$-, $[PF_6]^-$-, acetate, nitrate, $HSO_4^-$-, $SO_4^{2-}$-ions (J. S. Wilkes, M. J. Zaorotko, J. Chem. Soc., Chem. Commun., 13, 1992, 965, B. Ellis, WO 9618459 A1 960620, 1996 J. Fuller, R. T. Carlin, H. C. de Long, D. Haworth, J. Chem. Soc., Chem. Commun., 3, 1994, 299).

A one-step method for producing ionic liquids is described in the European patent application EP 00118442.3, and a method for halide-free production is described in the European patent application EP 00118441.5.

Ionic liquids, their properties and production can also be found P. Wasserscheid in Nachrichten aus der Chemie [Chemistry News], 2001 (49), pp. 12–16 and P. Wasserscheid and W. Keim in Angewandte Chemie [Applied Chemistry], 2000 (112), 3926–3945.

With the exception of one case, the cations used to date in ionic liquids have no chiral centers. The only ionic liquid with chirality in the cation [N,N-di-(2'S-2'-methanbutane) imidazolizumbromide] was described by Howarth et al. (J. Howarth, K. Hanlon, D. Fayne, P. McCormac, Tetrahedron Letters 1997, 17, 3097–3100). This chiral ionic liquid has an imidazolium ion with a chiral side chain and was used in the catalysed asymmetric Diels-Alder reaction, which lead however to minimal enantiomer excesses only. This class of chiral ionic liquids is very expensive to synthesise enantiomer-pure or enantiomer-enriched, because an enantiomer-pure or an enantiomer-enriched chlorine compound or another enantiomer-pure or an enantiomer-enriched alkylating agent has to be used as a preliminary step.

The object of the present invention is to provide ionic liquids which can be used in methods for asymmetric synthesis, in asymmetric catalysis and in separation of racemates.

In a further aspect of the invention a method for synthesis of chiral ionic liquids is to be provided which is improved compared to the prior art.

In a first aspect the invention relates to chiral ionic liquids of the general formula

whereby n=1 or 2,
the anion $[Y]^{n-}$ is the anion of an organic or inorganic proton acid and the cation $[A]^+$ is an optically active organic ammonium cation with up to 50 carbon atoms and at least one chirality center and at least one functional group, whereby the functional group can produce a coordination by forming hydrogen bridges or providing free electron pairs and at least one chirality center has a distance of up to 5 atomic bonds from the functional group.

The chiral ionic liquids according to the present invention have a melting point of up to 100° C. and preferably up to 80° C.

Basically, any proton acid can be considered as a proton acid whose anion can form the anion $[Y]^{n-}$, but particularly those with an acid constant $pk_s \leq 13$, preferably with an acid constant $pk_s \leq 8$, particularly preferably with an acid constant $pk_s \leq 5$.

The chiral ionic liquids according to the present invention can also comprise mixtures of the above-mentioned cations and anions, in particular a mixture of at least two different cations and an anion, a cation and at least two different anions or at least two different anions and at least two different anions.

In an embodiment the chiral ionic liquids according to the present invention are characterized in that the anion $[Y]^{n-}$ of the organic or inorganic proton acid is selected from the group comprising fluoride, chloride, bromide, iodide, nitrate, $HSO_4^-$, $H_2PO_4^-$, $HPO_4^{2-}$, bis-(trifluoromethane sulfone)-imidate, tetrafluoroborate ($[BF_4]^-$), tetrachloroborate ($[BCl_4]^-$), hexafluorophosphate ($[PF_6]^-$), hexafluoroantimonate ($[SbF_6]^-$), hexafluoroarsenate ($[AsF_6]^-$), tetrachloroaluminate ($[AlCl_4]^-$), trichlorozincate $[(ZnCl_3]^-)$, dichlorocuprate, sulfate ($[SO_4]^{2-}$), carbonate ($[CO_3]^{2-}$), fluorosulfonate, $[R'—COO]^-$, $[R'—SO_3]^-$ or $[(R'—SO_2)_2 N]^-$, whereby R' is a linear or branched aliphatic or alicyclic alkyl or $C_5$–$C_{18}$ aryl, $C_5$–$C_{18}$-aryl-$C_1$–$C_6$-alkyl or $C_1$–$C_6$-alkyl-$C_5$–$C_{18}$-aryl radical containing 1 to 12 carbon atoms, which may be substituted by halogen atoms, in particular fluoride and chlorine. The R' group can have at least one chirality center. Corresponding optically active starting compounds are to be assumed in this case. Examples of anions of the general formula R'—COO⁻ are butanoate, hexanoate, citrate, tartrate, lactate or succinate anions.

The chiral (optically active) ammonium cation [A]⁺ containing at least one chirality center has preferably up to 40, particularly preferably up to 25 carbon atoms, preferably at least 3, particularly preferably at least 5 carbon atoms.

The cation [A]⁺ preferably also has one alcohol (OH), ether (OR), thiol (SH), thioether (SR), nitrile (CN), carbonic acid- (COOH), carbonic acid ester (COOR), phosphane ($PR_2$), ketone (COR), aldehyde (CHO), nitro ($NO_2$), azide ($N_3$), phenyl, fluoride or chloride group as functional group G. These groups can form hydrogen bridges or provide free electron pairs for a coordination with other molecules, which have hydrogen bridge acceptors and/or acceptors for free electron pairs. At least one chirality center has a distance of 1 to 5 atomic bonds, preferably up to three atomic bonds from the functional group.

The ammonium cation [A]⁺ can be reproduced as general formula $[NR^wR^xR^yR^z]^+$,
whereby
$R^w$, $R^x$, $R^y$ and $R^z$ are selected independently of one another from the group comprising hydrogen;

linear or branched, saturated or unsaturated, aliphatic or alicyclic alkyl groups with 1 to 30 carbon atoms, preferably up to 20, particularly preferably up to 8 carbon atoms;

heteroaryl, heteroaryl $C_1$–$C_6$ alkyl groups with 3 to 8 carbon atoms in the heteroaryl radical and at least one heteroatom selected from N, O and S, which can be substituted with at least one group selected from $C_1$–$C_6$-alkyl groups and/or halogen atoms;

aryl, aryl $C_1$–C6 alkyl groups with 5 to 12 carbon atoms, preferably up to 10 carbon atoms in the aryl radical, and silyl groups of the general formula —SiR'R"R'", whereby R', R" and R'" are selected independently of one another from the group comprising $C_1$–$C_6$ alkyl and $C_5$–$C_{12}$ aryl, preferably $C_1$–$C_3$ alkyl;

whereby at least one of these $R^w$, $R^x$, $R^y$ and $R^z$ groups has at least one chirality center, at least one of the $R^w$, $R^x$, $R^y$ and $R^z$ groups is either substituted with at least one above-mentioned functional group or contains this, two of the $R^w$, $R^x$, $R^y$ and $R^z$ groups can be linked by forming a 4, 5, 6 or 7-member saturated or unsaturated ring, which can in addition contain at least one heteroatom selected from nitrogen, oxygen or sulphur, and this ring can be substituted by at least one of the above-mentioned alkyl, aryl or heteroaryl groups;

provided that not more than one, preferably not more than two, particularly preferably not more than three of the $R^w$, $R^x$, $R^y$ and $R^z$ groups are at the same time hydrogen. In a particularly preferred configuration chiral ionic liquids according to the present invention are characterized in that [A]⁺ is selected from the group comprising

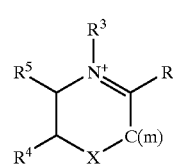

(I)

-continued

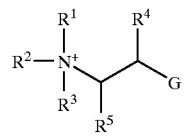

(II)

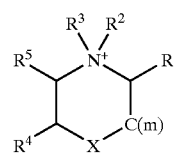

(III)

whereby m=0 or 1,
X is selected from the group comprising nitrogen, oxygen and sulphur, R, $R^1$, $R^2$, $R^3$, $R^4$ and $R^5$ are selected independently of one another from the group comprising hydrogen;

linear or branched, saturated or unsaturated, aliphatic or alicyclic alkyl groups with 1 to 30 carbon atoms, whereby the linear or branched aliphatic alkyl groups may be substituted by a hydroxyl or thiol group;

heteroaryl-, heteroaryl-$C_1$–$C_6$-alkyl groups with 3 to 8 carbon atoms in the heteroaryl radical and at least one heteroatom selected from N, O and S, which may be substituted by at least one group selected from $C_1$–$C_6$ alkyl groups and/or halogen atoms;

aryl, aryl $C_1$–$C_6$ alkyl groups with 5 to 12 carbon atoms in the aryl radical, which may be substituted optionally by at least one $C_1$–$C_6$ alkyl group and/or one halogen atom, and silyl groups of the general formula —$SiR^6R^7R^8$, whereby $R^6$, $R^7$ and $R^8$ are selected independently of one another from the group comprising $C_1$–$C_6$ alkyl and $C_5$–$C_{12}$ aryl, preferably $C_1$–$C_3$ alkyl, as well as G is selected from the group comprising —OH, ether (—OR), thiol, thioether (—SR), nitrile (—CN), carbonic acid (—COOH), carbonic acid ester (—COOR), phosphane (—$PR_2$), ketone (—COR), aldehyde (—CHO), nitro (—$NO_2$), azide (—$N_3$), phenyl, fluoride or chloride, whereby R has the above-mentioned meanings, provided that $R^4$ and $R^5$ is not simultaneously hydrogen.

The linear or branched, saturated or unsaturated, aliphatic or alicyclic alkyl groups preferably have up to 20 carbon atoms, particularly preferably up to 8 carbon atoms and are selected for example from the group comprising methyl, ethyl, propyl, isopropyl, n, iso, sec., tert.-butyl, the various isomers of the pentyl, hexyl, heptyl and octyl groups, which may be substituted optionally by a hydroxyl group, as well as the corresponding unsaturated and or cyclic groups, as long as they exist. In a preferred configuration R, $R^1$, $R^2$, $R^3$, $R^4$ and $R^5$ are hydrogen or the above-mentioned alkyl groups independently of one another.

In another alternative of the invention the chiral ionic liquids are characterized in that R, $R^1$, $R^2$, $R^3$, $R^4$, $R^5$, $R^6$, $R^7$ and $R^8$ can have at least one chirality center independently of one another.

Unless otherwise specified "halogen atom" or "halide" means fluor(ide), chlor(ide), brom(ide) or iod(ide), preferably fluoride, chloride or bromide.

"$C_1$–$C_6$ alkyl groups" refer to linear, branched or alicyclic groups, but in particular methyl, ethyl, n-propyl, iso-propyl, n-butyl, iso-butyl, sec.-butyl or tert.-butyl group. "$C_5$–$C_{12}$ aryl group" is understood to mean in particular the phenyl or the naphthyl group.

In another aspect the invention relates to a method for producing the above-mentioned chiral ionic liquids. The method according to the present invention allows substantially simpler and more cost-effective access to ionic liquids with chiral cations. This is enabled by a novel concept for synthesis of chiral ionic liquids. In the process the chirality in the alkylation step is introduced to the cation, but not as it is in the chiral ionic liquids published by Howarth et al. Neither are the ammonium, phosphonium, pyridinium or imidazolium cations generally employed for synthesis of ionic liquids used here, as previously.

In detail the invention relates to a method for producing the above-mentioned chiral ionic liquids by alkylation of an amine $NR^xR^yR^z$ based on the ammonium cation $[A]^+$ of the general formula $[NR^wR^xR^yR^z]^+$ with an alkylation reagent of the formula $R^wX^1$, $R^wSO_4R^w$, $R'SO_3R^w$ or $[R^w{}_3O]^+BF_4^-$, whereby $X^1$ is fluoride, chloride, bromide or iodide, $R^w$ has the meaning as given hereinabove, but is not hydrogen, $R^x$, $R^y$ and $R^z$ have the meanings as given hereinabove, provided that not more than two, preferably not more than one of the $R^x$, $R^y$ and $R^z$ groups are hydrogen at the same time.

The above-used term "alkylation" is to be replaced by "(hetero)arylation" or "silylation" according to context, if the corresponding above-mentioned groups are introduced.

In a particular configuration the invention relates to a method for producing the above-mentioned chiral ionic liquids by conversion [alkylation, (hetero)arylation or silylation] of the optically active amines

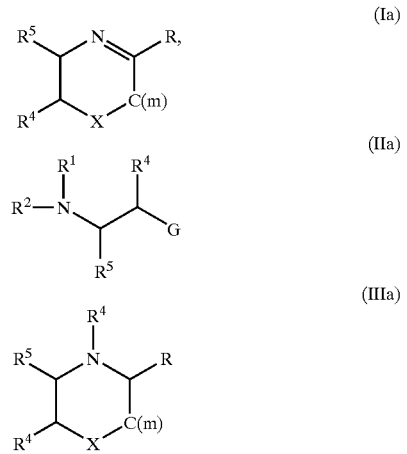

with a reagent [alkylation reagent, (hetero)arylation reagent, silylation reagent) of the formula $R^3X^1$, $R^3SO_4R^{3'}$, $R'SO_3R^3$ or $[R^3{}_3O]^+BF_4^-$, whereby $X^1$ is flouride, chloride, bromide or iodide, R' has the meaning given hereinabove, $R^3$ has the meaning given hereinabove and $R^{3'}$ is selected from the group of $R^3$, though it may be different to $R^3$.

Preferred is $R^3=R^{3'}$.

Di-$R^3$ sulphates of the general formula $R^3$—$SO_4$—$R^3$ are preferably used, and also symmetric organodisulfates in which $R^3$ has the meaning given hereinabove. Di-$C_1$–$C_6$ alkylsulfates are preferred, in particular dimethyl, diethyl, di-n-propyl, diisopropyl, di-n-butyl, diisobutyl, di-tert.-butyl, di-n-pentyl, diisopentyl, di-neo-pentyl, di-n-hexyl sulfate as well as dicyclohexyl sulfate. In addition, $C_1$–$C_6$ alkyl iodides and bromides as well as $[(C_1$–$C_6$—$)_3O]^+BF_4^-$ Meerwein are preferably salts.

In a subsequent reaction step the anion $X^{1-}$, $R^{3'}SO_4^-$, $R'SO_3^-$ and $BF_4^-$ can be transferred to an anion $[Y]^-$ or $[Y]^{2-}$ different thereto using exchange reactions known from the literature.

The optically active amines Ia, IIa and IIIa are known from the prior art, can be obtained commercially or can easily be manufactured without using known synthesis methods. Examples of starting products are compounds which are derived from amino acids, oxazoline, dihydroimidazoline, thiazoline, dihydrothiazoline, nicotine, ephedrine, 2-hydroxyalkylamine, 2-alkoxyalkylamine, etc. The optical purity of the ionic liquids according to the present invention is substantially dependent on the optical purity of the chiral starting compounds.

According to the present invention and in contrast to the chiral ionic liquids described by Howarth et al no expensive enantiomer-pure or enantiomer-enriched alkylation reagent is required for synthesis of the chiral ionic liquids in enantiomer-pure or enantiomer-enriched form. Rather, according to the present invention all cations are accessible via simple, organic synthesis steps known in the literature directly from naturally available, enantiomer-pure starting materials in enantiomer-pure or enantiomer-enriched form ("chiral pool"). The novel chiral ionic liquids are accessible in large quantities in enantiomer-pure or enantiomer-enriched form.

The reaction is performed at temperatures of −196° C. to +150° C., preferably between −80° C. and +80° C., quite particularly preferably between 0° C. and +60° C. Production and processing of the ionic liquids can be undertaken in suitable solvents or in substance.

The method for producing ionic liquids including anion exchange are dependent on individual systems and are known in the prior art. Reference can also be made to the literature cited in the introduction.

The above-mentioned chiral ionic liquids according to the present invention can by utilized to separate racemates into individual enantiomers, as solvents for asymmetric inorganic and organic synthesis, and also as solvent for asymmetric catalysis in organic and inorganic reactions.

The racemates are separated by formation of a dual-phase system, whereby one phase is formed by the racemate, and the other is formed by the chiral ionic liquid. Conditional on the varying solubility of the enantiomers in the chiral ionic liquid, there is enriching of the better soluble enantiomer in the chiral ionic liquid.

Alternatively, the racemate can be dissolved in a suitable solvent. This solution of the racemate then forms the two-phase system with the chiral ionic liquid. Again conditional on the varying solubility of the enantiomer in the chiral ionic liquid there is enriching of the enantiomer better soluble in the chiral ionic liquid in this chiral ionic liquid.

Accordingly, the chiral ionic liquids according to the present invention can be used as chlatrate former in racemate splitting or enantiomer separation via extractive crystallisation or as solvent for extractive racemate splitting or enantiomer separation.

Further areas of application of the ionic liquids according to the present invention are to be seen in their use as solvent for asymmetric organic and inorganic synthesis, for example in Diels-Alder reactions and benzoin reactions and asymmetric catalysis, in particular in hydration and hydrovinylation.

Accordingly, the invention also relates to methods for racemate splitting and enantiomer separation, asymmetric synthesis and for asymmetric catalysis using the chiral ionic liquids according to the invention.

Racemate separation, asymmetric synthesis and asymmetric catalysis take place in the presence of the chiral ionic liquids according to the present invention with high enantiomer yields.

The following examples serve to clarify the invention without limiting it in any way.

EXAMPLES 1H and 13C NMR spectroscopic conditions were carried out with a NMR spectrometer DPX 300 by Bruker.

The enantiomer excess was determined by deriving the resulting chiral ionic liquid with Mosher's reagent and subsequent NMR spectroscopic evaluation of the enantiomer peaks.

(1) Synthesis of the Chiral Ionic Liquid 4-(S)-Isopropyl-2,3-dimethyl-oxazoliniumtetrafluoroborate 117 g (1 mol) L-valine are suspended with 100 g (2.5 mol) sodium borhydride in 1000 ml THF and cooled to 0° C. A solution of 66 ml (1.25 mol) sulphuric acid in 150 ml diethyl ether is added with stirring, such that the temperature of the reaction mixture remains below 20° C. When addition is complete the whole is heated to room temperature and stirred for 12 h. To destroy excess diborane 100 ml methanol are added. The reaction mixture is concentrated on the rotation evaporator to around 500 ml and 1000 ml 5N sodium hydroxide solution added. The solvents are distilled to 100° C., then cooked for 3 h under reflux. The solution is extracted with dichloromethane, and the dichloromethane is removed under vacuum. The valinol yield is 86.5 g (84%).

20 g (0.194 mol) valinol are dissolved with 11.64 g (0.194 mol) acetic acid in 60 ml toluol and cooked for 24 h under reflux in the water separator. After cooling the solution is extracted with 10% hydrochloric acid. The aqueous phase is neutralized with 40% sodium hydroxide solution and extracted with diethyl ether. The organic phase is dried via $Na_2SO_4$ and the solvent removed. Distillation (112° C.) produces 19.2 g (78%) 4-(S)-isopropyl-2-methyloxazoline as a colourless oil.

15 g (0.12 mol) 4-(S)-isopropyl-2-methyloxazoline are dissolved in 50 ml dichloromethane and cooled to −20° C. 18 g (0.122 mol) Meerwein's reagent are added portionwise. The reaction mixture is stirred for 2 h at room temperature after addition is completed. The solvent is removed under vacuum and the residue is washed with diethyl ether. The yield of 4-(S)-isopropyl-2,3-dimethyl-oxazoliniumtetrafluoroborate is 27 g. The enantiomer excess in the product is >95%.

NMR Data:

$^1$H-NMR ($CDCl_3$): 5.22 (ddd, 1H); 4.69 (d, 2H); 3.53 (s, 3H); 2.41 (m, 1H); 2.17 (s, 3H); 0.99 (d, 3H); 0.93 (d, 3H).

$^{13}$C-NMR ($CDCl_3$): 176.4; 72.1; 68.4; 53.8; 26.7; 18.0; 15.6; 15.0.

(2) Synthesis of the Chiral Ionic Liquid 3-Butyl-4-(S)-isopropyl-2-methyl-oxazoliniumtetrafluoroborate 117 g (1 mol) L-valine are suspended with 100 g (2.5 mol) sodium borhydride in 1000 ml THF and cooled to 0° C. A solution of 66 ml (1.25 mol) sulphuric acid in 150 ml diethyl ether is added with stirring, such that the temperature of the reaction mixture remains below 20° C. When addition is complete the whole is heated to room temperature and stirred for 12 h. To destroy excess diborane 100 ml methanol are added. The reaction mixture is concentrated on the rotation evaporator to around 500 ml and 1000 ml 5N sodium hydroxide solution added. The solvents are distilled to 100° C., then cooked for 3 h under reflux. The solution is extracted with dichloromethane, and the dichloromethane is removed under vacuum. The valinol yield is 86.5 g (84%).

20 g (0.194 mol) valinol are dissolved with 11.64 g (0.194 mol) acetic acid in 60 ml toluol and cooked for 24 h under reflux in the water separator. After cooling the solution is extracted with 10% hydrochloric acid. The aqueous phase is neutralized with 40% sodium hydroxide solution and extracted with diethyl ether. The organic phase is dried via $Na_2SO_4$ and the solvent removed. Distillation (112° C.) produces 19.2 g (78%) 4-(S)-isopropyl-2-methyloxazoline as a colourless oil.

15 g (0.12 mol) 4-(S)-isopropyl-2-methyloxazoline are dissolved in 50 ml dichloromethane and mixed with 17.8 g (0.13 mol) butyl bromide are added at room temperature with stirring. After addition is finished this is heated for 2 h at 50° C. After the solvent is removed under vacuum 31.4 g (99%) 3-butyl-4-(S)-isopropyl-2-methyl-oxazoliniumbromide is obtained.

This is dissolved in 50 ml dichloromethane and mixed with 22 g (0.2 mol) sodium-tetrafluoroborate. This mixture is stirred for 5 days at room temperature. The salts are filtered off and the solvent removed under vacuum. The 3-butyl-4-(S)-isopropyl-2-methyloxazoliniumtetrafluoroborate yield is 29.5 g. The enantiomer excess in the product is >95%.

NMR Data:

$^1$H-NMR ($CDCl_3$): 5.13 (ddd, 1H); 4.72 (dd, 2H); 4.42 (t, 2H); 2.43 (m, 1H); 2.22 (s, 3H); 1.99 (tt, 2H); 1.39 (tt, 2H); 1.05 (d, 3H). 0.99 (t, 3H); 0.95 (d, 3H).

$^{13}$C-NMR ($CDCl_3$): 175.3; 71.0; 67.8; 54.3; 50.1; 31.4; 25.5; 19.2; 17.2; 14.8; 12.9.

(3) Synthesis of the Chiral Ionic Liquid 3-Butyl-4-(S)-isopropyl-2-methyloxazoliniumhexafluorophosphate 117 g (1 mol) L-valine are suspended with 100 g (2.5 mol) sodium borhydride in 1000 ml THF and cooled to 0° C. A solution of 66 ml (1.25 mol) sulphuric acid in 150 ml diethyl ether is added with stirring, such that the temperature of the reaction mixture remains below 20° C. When addition is complete the whole is heated to room temperature and stirred for 12 h. To destroy excess diborane 100 ml methanol are added. The reaction mixture is concentrated on the rotation evaporator to around 500 ml and 1000 ml 5N sodium hydroxide solution added. The solvents are distilled to 100° C., then cooked for 3 h under reflux. The solution is extracted with dichloromethane, and the dichloromethane is removed under vacuum. The valinol yield is 86.5 g (84%).

20 g (0.194 mol) valinol are dissolved with 11.64 g (0.194 mol) acetic acid in 60 ml toluol and cooked for 24 h under reflux in the water separator. After cooling the solution is extracted with 10% hydrochloric acid. The aqueous phase is neutralized with 40% sodium hydroxide solution and extracted with diethyl ether. The organic phase is dried via $NaSO_4$ and the solvent removed. Distillation (112° C.) produces 19.2 g (78%) 4-(S)-isopropyl-2-methyloxazoline as a colourless oil.

15 g (0.12 mol) oxazoline are dissolved in 50 ml dichloromethane and mixed with 17.8 g (0.13 mol) butyl bromide are added at room temperature with stirring. After addition is finished this is heated for 2 h at 50° C. After the solvent is removed under vacuum 31.4 g (99%) 3-butyl-4-(S)-isopropyl-2-methyl-oxazoliniumbromide is obtained.

20 g (0.074 mol) oxazolinium salt are dissolved in 100 ml water and mixed at room temperature with stirring with 0.1 mol hexafluorophosphoric acid in an aqueous solution. The reaction mixture is washed repeatedly with water and the solvent is removed under vacuum. The yield of 3-butyl-4-(S)-isopropyl-2-methyl-oxazoliniumhexafluorophosphate is 24 g. The enantiomer excess in the product is >95%.

NMR Data:

$^1$H-NMR (CDCl$_3$): 5.22 (ddd, 1H); 4.69 (dd, 2H); 4.40 (t, 2H); 2.41 (m,1H); 2.17 (s, 3H); 1.93 (tt, 2H); 1.35 (tq, 2H); 0.99 (d, 3H), 0.96 (t, 3H); 0.93 (d, 3H).

$^{13}$C-NMR (CDCl$_3$): 176.4; 72.1; 68.4; 53.8; 49.6; 32.1; 26.7; 19.4; 18.0; 15.0; 13.4.

(4) Synthesis of the Chiral Ionic Liquid (1-Hydroxymethyl-2-methyl-propyl)-trimethylammonium-hexafluorophosphate 117 g (1 mol) L-valine are suspended with 100 g (2.5 mol) sodium borhydride in 1000 ml THF and cooled to 0° C. A solution of 66 ml (1.25 mol) sulphuric acid in 150 ml diethyl ether is added with stirring, such that the temperature of the reaction mixture remains below 20° C. When addition is complete the whole is heated to room temperature and stirred for 12 h. To destroy excess diborane 100 ml methanol are added. The reaction mixture is concentrated on the rotation evaporator to around 500 ml and 1000 ml 5N sodium hydroxide solution added. The solvents are distilled to 100° C., then cooked for 3 h under reflux. The solution is extracted with dichloromethane, and the dichloromethane is removed under vacuum. The valinol yield is 86.5 g (84%).

58.5 g (0.5 mol) valinol are dissolved in 115 g (2.5 mol) formic acid and cooled to 0° C. 1.2 mol formaldehyde are added to this mixture and heated until carbon dioxide formation is complete on the boiling water bath. The solution is acidified with hydrochloric acid and the solvents removed by vacuum. The residue is dissolved in 50 ml water, made basic with 25% sodium hydroxide solution and extracted with diethyl ether. The extracts are dried via sodium sulfate and the solvent removed under vacuum. Distillation (33 mbar/80° C.) yields 53.7 g (82%) N,N-dimethylvalinol as a colourless oil. 50 g (0.38 mol) N,N-dimethylvalinol are dissolved in 100 ml dichloromethane, mixed with 56.8 g (0.4 mol) methyl iodide and stirred at room temperature for 12 h. The solvent is removed under vacuum, the residue is dissolved in 200 ml water and mixed with ice cooling with 0.4 mol hexafluorophosphoric acid in an aqueous solution. The reaction mixture is washed repeatedly with water and the solvent removed under vacuum. The yield of (1-hydroxymethyl-2-methyl-propyl)-trimethylammonium-hexafluorophosphate is 107 g. The enantiomer excess in the product is >95%.

What is claimed is:

1. Chiral ionic liquids of the general formula

[A]$_n^+$[Y]$^{n-}$, wherein n=1 or 2, the anion [Y]$^{n-}$ is the anion of an organic or inorganic proton acid and the cation [A]$^+$ is an optically active organic ammonium cation with up to 50 carbon atoms and at least one chirality center and at least one functional group selected from the group comprising alcohol (OH), ether (OR), thiol (SH), thioether (SR), nitrile (CN), carboxylic acid- (COOH), carboxylic acid ester (COOR), phosphane (PR$_2$), ketone (COR), aldehyde (CHO), nitro (NO$_2$), azide (N$_3$), phenyl, fluoride or chloride, wherein R is selected from the group consisting of hydrogen;

linear or branched, saturated or unsaturated, aliphatic or alicyclic alkyl groups with 1 to 30 carbon atoms, whereby the linear or branched aliphatic alkyl groups may be substituted by a hydroxyl or thiol group;

heteroaryl-, heteroaryl-C$_1$–C$_6$-alkyl groups with 3 to 8 carbon atoms in the heteroaryl radical and at least one heteroatom selected from N, O and S, which may be substituted by at least one group selected from C$_1$–C$_6$ alkyl groups and halogen atoms;

aryl, aryl C$_1$–C$_6$ alkyl groups with 5 to 12 carbon atoms in the aryl radical, which may be substituted optionally by at least one C$_1$–C$_6$ alkyl group and one halogen atoms, and silyl groups of the general formula —SiR$^6$R$^7$R$^8$, whereby R$^6$, R$^7$ and R$^8$ are selected independently of one another from the group consisting of C$_1$–C$_6$ alkyl and C$_5$–C$_{12}$ aryl wherein said functional group produces a coordination by forming hydrogen bridges or providing free electron pairs and said at least one chirality center has a distance of up to 5 atomic bonds from said functional group.

2. Chiral ionic liquids as claimed in claim 1, comprising a mixture of at least two different cations and anions.

3. Chiral ionic liquids as claimed in claim 2, wherein the anion [Y]$^{n-}$ of the organic proton acid is selected from the group consisting of fluoride, chloride, bromide, iodide, nitrate, HSO$_4^-$, H$_2$PO$_4^-$, HPO$_4^{2-}$, bis-(trifluoromethane sulfone)-imidate, tetrafluoroborate ([BF$_4$]$^-$), tetrachloroborate ([BCl$_4$]$^-$), hexafluorophosphate ([PF$_6$]$^-$), hexafluoroantimonate ([SbF$_6$]$^-$), hexafluoroarsenate ([AsF$_6$]$^-$), tetrachloroaluminate ([AlCl$_4$]$^-$), trichlorozincate [(ZnCl$_3$]$^-$), dichlorocuprate, sulfate ([SO$_4$]$^{2-}$), carbonate ([CO$_3$]$^{2-}$), fluorosulfonate, [R'—COO]$^-$, [R'—SO$_3$]$^-$ or [(R'—SO$_2$)$_2$N]$^-$, whereby R' is a linear or branched aliphatic or alicyclic alkyl or C$_5$–C$_{18}$ aryl, C$_5$–C$_{18}$-aryl-C$_1$–C$_6$-alkyl or C$_1$–C$_6$-alkyl-C$_5$–C$_{18}$-aryl radical containing 1 to 12 carbon atoms, which may be substituted by halogen atoms.

4. Chiral ionic liquids as claimed in claim 3, wherein the R' group has least one chirality center.

5. Chiral ionic liquids as claimed in claim 1, wherein [A]$^+$ is selected from the group consisting of

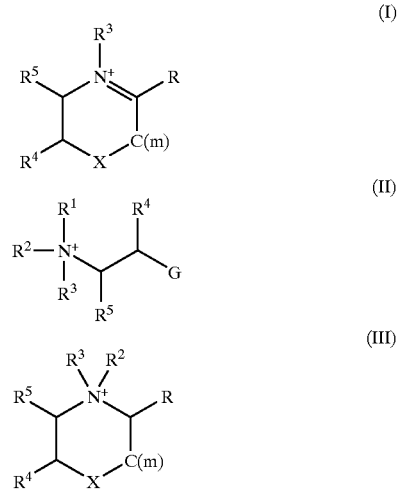

wherein m=0 or 1,

X is selected from the group consisting of nitrogen, oxygen and sulphur,

R, R$^1$, R$^2$, R$^3$, R$^4$ and R$^5$ are selected independently of one another from the group consisting of hydrogen;

linear or branched, saturated or unsaturated, aliphatic or alicyclic alkyl groups with 1 to 30 carbon atoms, whereby the linear or branched aliphatic alkyl groups may be substituted by a hydroxyl or thiol group;

heteroaryl, heteroaryl $C_1$–$C_6$ alkyl groups with 3 to 8 carbon atoms in the heteroaryl radical and at least one heteroatom selected from N, O and S, which may be substituted by at least one group selected from $C_1$–$C_6$ alkyl groups and/or halogen atoms;

aryl, aryl $C_1$–$C_6$ alkyl groups with 5 to 12 carbon atoms in the aryl radical, which may be substituted optionally by at least one $C_1$–$C_6$ alkyl group and/or one halogen atom, and silyl groups of the general formula —$SiR^6R^7R^8$, whereby $R^6$, $R^7$ and $R^8$ are selected independently of one another from the group consisting of $C_1$–$C_6$ alkyl and $C_5$–$C_{12}$ aryl, and G is selected from the group consisting of —OH, ether (—OR), thiol, thio-ether (—SR), nitrile (—CN), carbonic acid (—COOH), carbonic acid ester (—COOR), phosphane (—$PR_2$), ketone (—COR), aldehyde (—CHO), nitro (—$NO_2$), azide (—$N_3$), phenyl, fluoride or chloride, whereby R has the above-mentioned meanings, provided that $R^4$ and $R^5$ are not simultaneously hydrogen.

6. Chiral ionic liquids as claimed in claim 5 wherein R, $R^1$, $R^2$, $R^3$, $R^4$, $R^5$, $R^6$, $R^7$ and $R^8$ can have at least one chirality center independently of one another.

7. Chiral liquid as claimed in claim 1 selected from the group consisting of 4-(S)-isopropyl-2,3-dimethyl-oxazoliniumtetrafluoroborate, 3-butyl-4-(S)-isopropyl-2-methyl-oxazoliniumtetrafluoroborate, 3-butyl-4-(S)-isopropyl-2-methyl-oxazolinium-hexafluorophosphate, (1-hydroxymethyl-2-methyl-propyl)-tri-methyl ammonium-hexafluorophosphate.

8. A method for producing the ionic liquids of claim 1 having an ammonium cation [A]+ of the formula [$NR^wR^xR^yR^z$]+ comprising the step of converting an amine, $NR^xR^yR^z$, with a reagent of the formula $R^wX^1$, $R^wSO_4R^w$, $R'SO_3R^w$ or [$R^w_3O$]$^+BF_4^-$, wherein $R^w$, $R^x$, $R^y$ and $R^z$ are selected independently of one another from the group consisting of hydrogen;

linear or branched, saturated or unsaturated, aliphatic or alicyclic alkyl groups with 1 to 30 carbon atoms;

heteroaryl, heteroaryl $C_1$–$C_6$ alkyl groups with 3 to 8 carbon atoms in the heteroaryl radical and at least one heteroatom selected from N, O and S, which can be substituted with at least one group selected from $C_1$–$C_6$-alkyl groups and/or halogen atoms;

aryl, aryl $C_1$–$C_6$ alkyl groups with 5 to 12 carbon atoms; and silyl groups of the general formula —$SiR'R''R'''$, wherein $R'$, $R''$ and $R'''$ are selected independently of one another from the group consisting of $C_1$–$C_6$ alkyl and $C_5$–$C_{12}$ aryl; $X^1$ is fluoride, chloride, bromide or iodide, and at least one of said $R^w$, $R^x$, $R^y$ and $R^z$ groups has at least one chirality center, at least one of the $R^w$, $R^x$, $R^y$ and $R^z$ groups is either substituted with at least one functional group of claim 1 or contains said at least one functional group, two of the $R^w$, $R^x$, $R^y$ and $R^z$ groups in said formula [$NR^wR^xR^yR^z$]$^+$ can be linked by forming a 4, 5, 6 or 7-member saturated or unsaturated ring, which can in addition contain at least one heteroatom selected from nitrogen, oxygen or sulphur, and said ring can be substituted by at least one alkyl, aryl or heteroaryl groups of claim 1, but $R^w$ is not hydrogen, provided that not more than two of the $R^x$, $R^y$ and $R^z$ groups are hydrogen at the same time.

9. The method for producing the ionic liquids as claimed in claim 8 by conversion of the optically active amines

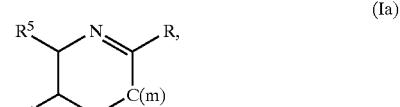

(Ia)

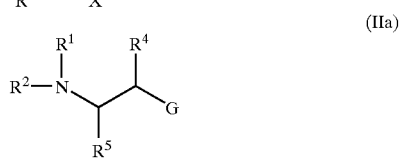

(IIa)

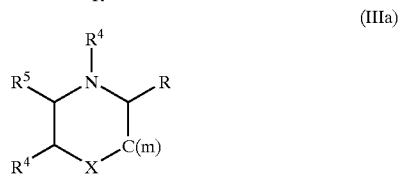

(IIIa)

with a reagent of the formula $R^3X^1$, $R^3SO_4R^{3'}$, $R'SO_3R^3$ or [$R^3_3O$]$^+BF_4^-$, whereby $X^1$ is fluoride, chloride, bromide or iodide, R' has the meaning given in claim 4, $R^3$ has the meaning given in claim 6 and $R^{3'}$ is selected from the $R^3$ group, but may be different to $R^3$.

10. The method as claimed in claim 8 wherein the reaction is carried out at temperatures of −196° C. to +150° C.

11. A process for separating racemates by contacting the racemates with the chiral ionic liquid of claim 1, resulting in the separation of the racemates due to the different solubilities of the racemates in the ionic liquid.

12. A process for asymmetric synthesis, comprising the step of contacting the materials to be synthesized with the chiral ionic liquids of claim 1.

13. A process for asymmetric catalysis comprising the step of contacting the materials to be catalyzed with the chiral ionic liquid of claim 1.

14. A method for separating enantiomer mixtures into their enantiomers in the presence of chiral ionic liquids, comprising the step of contacting the mixture with the chiral ionic liquid of claim 1 to form more soluble enantiomer and less soluble enantiomer layers in the ionic liquid.

15. The method as claimed in claim 14, including the additional step of dissolving the enantiomer mixture in a solvent prior to the step of contacting the enantiomer mixture with the ionic liquid of claim 1.

16. The method for enriching an enantiomer in an enantiomer mixture by placing the enantiomer mixture in contact with the chiral ionic liquid of claim 7.

17. The method as claimed in claim 16, wherein the enantiomer mixture used is dissolved in a solvent.

18. The method for asymmetric synthesis comprising the step of employing as a solvent the chiral ionic liquids of claim 1.

19. The method as claimed in claim 18, wherein the method of synthesis is selected from the group consisting of a Diels-Alder reaction or a benzoin synthesis.

20. The method of asymmetric catalysis comprising the step of carrying out the catalysis in the presence of at least one chiral ionic liquid, as defined in claim 1.

21. The method as claimed in claim 20, wherein catalysis is carried out by hydration.

22. Chiral ionic liquids as claimed in claim 1 characterized in that the ammonium cation [A]$^+$ has the general formula [$NR^wR^xR^yR^z$]$^+$, wherein $R^w$, $R^x$, $R^y$ and $R^z$ are selected independently of one another from the group consisting of hydrogen;

linear or branched saturated or unsaturated, aliphatic or alicyclic alkyl groups with 1 to 30 carbon atoms;

heteroaryl, heteroaryl $C_1$–$C_6$ alkyl groups with 3 to 8 carbon atoms in the heteroaryl radical and at least one heteroatom selected from N, O and S, which can be substituted with at least one group selected from $C_1$–$C_6$-alkyl groups and/or halogen atoms;

aryl, aryl $C_1$–$C_6$ alkyl groups with 5 to 12 carbon atoms; and silyl groups of the general formula —$SiR^tR^uR^v$, wherein $R^t$, $R^u$ and $R^v$ are selected independently of one another from the group consisting of $C_1$–$C_6$ alkyl and $C_5$–$C_{12}$ aryl;

and at least one of said $R^w$, $R^x$, $R^y$ and $R^z$ groups has at least one chirality center, at least one of the $R^w$, $R^x$, $R^y$ and $R^z$ groups is either substituted with at least one functional group of claim 1 or contains said at least one functional group, two of the $R^w$, $R^x$, $R^y$ and $R^z$ groups in said formula [$NR^wR^xR^yR^z$] can be linked by forming a 4, 5, 6 or 7-member saturated or unsaturated ring, which can in addition contain at least one heteroatom selected from nitrogen, oxygen or sulphur, and said ring can be substituted by at least one alkyl, aryl or heteroaryl groups of claim 1, provided that not more than three of the $R^w$, $R^x$, $R^y$ and $R^z$ groups are hydrogen at the same time.

\* \* \* \* \*